United States Patent [19]

Classey et al.

[11] Patent Number: 5,290,239
[45] Date of Patent: Mar. 1, 1994

[54] INTRAVENOUS TUBE SAFETY APPARATUS

[75] Inventors: Donald J. Classey, Waukegan; Theresa Grajo, Round Lake Beach; Kenneth Lynn, McHenry; John McVey, Lake Zurich; Eric Myren, Barrington; Gabriel Vehovsky, McHenry, all of Ill.

[73] Assignee: Baxter International, Inc., Deerfield, Ill.

[21] Appl. No.: 884,498

[22] Filed: May 15, 1992

Related U.S. Application Data

[63] Continuation-in-part of Ser. No. 826,273, Jan. 17, 1992, which is a continuation of Ser. No. 765,755, Sep. 26, 1991, abandoned.

[51] Int. Cl.$^5$ .............................. A61M 37/00
[52] U.S. Cl. .................. 604/131; 128/DIG. 12
[58] Field of Search .............. 604/131, 250, 151; 128/DIG. 12, DIG. 13; 251/7

[56] References Cited

U.S. PATENT DOCUMENTS

| | | |
|---|---|---|
| D. 200,729 | 3/1965 | Coanda . |
| D. 230,729 | 3/1974 | Zeddies . |
| D. 233,312 | 10/1974 | Lock . |
| 2,092,400 | 9/1937 | Miller . |
| 2,503,327 | 4/1950 | Fields . |
| 2,715,905 | 8/1955 | Ogle . |
| 2,775,240 | 12/1956 | Morrisey, Jr. et al. . |
| 2,889,848 | 6/1959 | Redmer . |
| 3,167,299 | 1/1965 | Ling . |
| 3,316,935 | 5/1967 | Kaiser et al. . |
| 3,357,674 | 7/1963 | Coanda et al. . |
| 3,374,509 | 3/1968 | Logan et al. . |
| 3,612,475 | 10/1971 | Dinger . |
| 4,137,940 | 2/1979 | Faisandier . |
| 4,155,362 | 5/1979 | Jess . |
| 4,248,401 | 2/1981 | Mittleman . |
| 4,307,869 | 12/1981 | Mittleman . |
| 4,367,736 | 1/1983 | Gupton . |
| 4,416,595 | 11/1983 | Cromib .............. 128/DIG. 12 |
| 4,434,963 | 3/1984 | Russell . |
| 4,439,179 | 3/1984 | Lueders et al. . |
| 4,460,358 | 7/1984 | Somerville et al. . |
| 4,519,792 | 5/1985 | Dawe .............. 128/DIG. 12 |
| 4,524,802 | 6/1985 | Lawrence et al. . |
| 4,565,542 | 1/1986 | Berg .............. 604/131 |
| 4,585,441 | 4/1986 | Archibald . |
| 4,586,691 | 5/1986 | Kozlow . |
| 4,637,817 | 1/1987 | Archibald et al. .......... 128/DIG. 3 |
| 4,689,043 | 8/1987 | Bisha . |
| 4,818,190 | 4/1989 | Pelmulder et al. . |
| 4,857,050 | 8/1989 | Lentz et al. . |
| 4,978,335 | 12/1990 | Arthur, III . |
| 5,009,641 | 4/1991 | Gorton .............. 604/131 |
| 5,017,192 | 5/1991 | Dodge et al. . |
| 5,039,279 | 8/1991 | Natwick et al. . |

*Primary Examiner*—Paul J. Hirsch
*Attorney, Agent, or Firm*—Wood, Phillips, VanSanten, Hoffman & Ertel

[57] ABSTRACT

The present invention provides an apparatus for use in a peristaltic pump 20 which prevents an inadvertent free flow condition prior to loading or after removal of an I.V. tube 26 in the peristaltic pump 20 and which also prevents the inadvertent occlusion of a loaded I.V. tube 26 in the peristaltic pump 20. A standard I.V. tube 26 has a slide clamp 109 provided thereon. The apparatus includes an I.V. tube groove 29 into which the I.V. tube 26 is positioned, a slide clamp receiving area 62 into which the slide clamp 109 is inserted, and a biased sliding member 81 which the inserted slide clamp 109 engages such that the I.V. tube 26 cannot be loaded into the apparatus without the slide clamp 109 occluding the I.V. tube 26. The present invention also contemplates a slide clamp 109' compatible with the apparatus having a surface pad 125 for facilitating automated identification of the slide clamp 109' in cooperation with a non-obstructive sensor 85 in the safety apparatus. The present invention further contemplates a slide clamp 109' having an I.V. tube receiving aperture 110' with an inner diameter profile which minimizes friction between I.V. tube contacting surfaces 126 of the aperture 110' as an I.V. tube 26 is slid transverse to its length within the aperture 110' and which has a surface pad 125 for facilitating automated identification of the slide clamp.

9 Claims, 13 Drawing Sheets

INTRAVENOUS TUBE SAFETY APPARATUS

CROSS-REFERENCE

This application is a continuation-in-part of application Ser. No. 826,273, filed Jan. 17, 1992, which is a continuation of application Ser. No. 765,755, filed Sep. 26, 1991 now abandoned.

FIELD OF THE INVENTION

The present invention relates in general to clamps used to control the flow of medical fluid to an I.V. tubing and, in particular, to a safety apparatus utilized in a peristaltic intravenous infusion pump.

BACKGROUND OF THE INVENTION

Administration of intravenous fluids to a patient is well known in the art. Typically, a solution such as saline, glucose or electrolyte in a glass or flexible container is fed to a patient's venous access site via a length of flexible plastic I.V. tubing such as polyvinyl chloride (PVC) tubing. The rate of flow of the fluid is controlled by a roller clamp which is adjusted to restrict the flow lumen of the I.V. tubing until the desired flow rate is obtained.

Flow from the container to the patient may also be regulated by means other than a roller clamp. It is becoming more and more common to use an electronically controlled pump. One type of pump that is used for intravenous fluid administration is a peristaltic-type pump.

Use of peristaltic pumping action is particularly well suited for the medical field. This is because peristaltic pumping action can be applied externally of the I.V. tubing carrying the intravenous fluid. This maintains the sterile condition of the intravenous fluid within the I.V. tubing while imparting fluid propulsion on the fluid. The peristaltic pumping action can also be applied on any point on the I.V. tubing.

In a common type of peristaltic pump used in the medical field, a driving motor is connected to an array of cams which are angularly spaced from each other. The cams in turn drive cam followers which are connected to corresponding pressure fingers. These elements cooperate to impart a linear wave motion on the pressure fingers. A pressure plate is secured juxtaposed to and spaced from the pressure fingers. The pressure plate holds the I.V. tubing against the reciprocating pressure fingers to impart the wave motion on the I.V. tubing to propel the fluid.

In another common type of peristaltic pump used in the medical field, a driving motor is connected via an armature to at least one roller member. The driving motor imparts a circular rotation on the armature which actuates the roller member. A semicircular pressure plate having the same center point as the armature is provided with the I.V. tubing located between the roller member and the pressure plate. The pressure plate holds the I.V. tubing against the roller member which imparts a circular motion on the I.V. tubing to propel the fluid.

One drawback of the use of peristaltic pumps is that, because when loaded into the pump the peristaltic action drives the propulsion of the fluid, prior to loading into the pump, the I.V. tubing is often left in an open condition. While a straightforward solution to this problem is to simply provide a roller or other flow clamp on the I.V. tubing to occlude the I.V. tubing prior to loading and after removal, this creates the possibility that the health care professional loading the I.V. tubing into the peristaltic pump will forget to open the I.V. tubing after loading has been completed. While a solution which includes a dedicated flow clamp and housing which is loaded into the peristaltic pump has been provided, this solution has several drawbacks, including the dedicated use of such a flow clamp assembly for a select peristaltic pump and the ease in which the locking mechanism can be bypassed manually by a health care professional. Moreover, because this solution employs a dedicated slide clamp, health care professionals must take care to remove the slide clamp before disposal of the I.V. tubing.

Prior art slide clamps generally include a regulating aperture defining an occluding slot and a non-occluding passage. An I.V. tube inserted through the regulating aperture in an operative position is slidable transverse to the length of the tube between the non-occluding passage and the occluding slot to control the flow of fluid through the lumen of the I.V. tube. With the I.V. tube in an operative position in the non-occluding passage, prior art slide clamps tend to slide longitudinally of the I.V. tube under the effect of gravity. Often, this sliding makes it difficult and cumbersome for medical personnel to quickly locate the slide clamp to occlude flow at a desired position along the length of the I.V. tube. In addition, the tube contacting surface of the flow regulating aperture typically extends over the entire depth of the slide clamp. As a result, prior art slide clamps leave a relatively wide surface contacting an I.V. tube in an operative position, providing a significant frictional force opposing sliding of an I.V. tube relative to the slide clamp between the non-occluding passage and the occluding slot. Both of these features make it relatively difficult to use prior art slide clamps with a safety mechanism for use in a peristaltic pump. First, it can be difficult for a health care professional to locate the slide clamp for insertion into a slide clamp receiving slot in the peristaltic pump and second, once inserted, prior art slide clamps may offer too much frictional resistance for the safety apparatus to drive the slide clamp between the occluded slot and the non-occluding passage.

What would thus be advantageous would be a safety mechanism for use in a peristaltic pump which utilizes a disposable I.V. slide clamp carried by I.V. tubing which can be located longitudinally of the tube and not displaced solely by force of gravity and which can be slid between a non-occluding passage and an occluded slot with minimal force. The safety mechanism would preferably prevent both an inadvertent free flow condition prior to loading or after removal of an I.V. tube in a peristaltic pump and prevent inadvertent occlusion of a loaded I.V. tube.

SUMMARY OF THE INVENTION

The present invention provides an apparatus for use in a peristaltic pump which prevents an inadvertent free flow condition prior to loading or after removal of an I.V. tube in a peristaltic pump and which also prevents the inadvertent occlusion of a loaded I.V. tube in a peristaltic pump. The present invention includes a standard I.V. tube having a slide clamp provided thereon. The apparatus includes an I.V. tube groove into which the I.V. tubing is positioned, a slide clamp receiving area into which the slide clamp is inserted, and a biased sliding member which the inserted slide clamp engages such that the I.V. tubing cannot be loaded into the apparatus without the slide clamp occluding the I.V. tubing.

The sliding member includes a cam portion which interacts with a cam follower on a pair of retainer arms which causes the retainer arms to pivot into an open position. Upon completing the loading of the slide clamp and I.V. tubing, the peristaltic pumping door is closed which 1) secures the I.V. tubing in the I.V. tube groove, 2) disengages the loaded sliding member which forces the slide clamp into a free flow or non-occluding state with respect to the I.V. tube, 3) engages the retaining arms which secures the now open slide clamp in the apparatus, and 4) positions a safety clamp in a ready but open state.

To unload the I.V. tube from the apparatus, the door is opened which causes the safety clamp to occlude the I.V tube. Prior to removal of the I.V. tube, the slide clamp must again be engaged into an occluded state with respect to the I.V. tube, thereby 1) reloading the slide member, 2) pivoting via the cam and cam followers the retainer arms into the open position and 3) freeing the safety clamp so that it can be positioned in the latched open position. It is only after these steps have been completed with the slide clamp occluding the I.V. tube that the I.V. tube and the slide clamp can be removed.

The present invention also provides a safety apparatus for preventing free flow of fluids through a flow lumen of an I.V. tube mounted to a pump, the safety apparatus including a clamp receiving the I.V. tube in an operative position, the clamp being selectively movable between a flow lumen occluding position wherein the clamp collapses a wall of the I.V. tube in the operative position, and a non-occluding position wherein the clamp does not collapse a wall of an I.V. tube in the operative position. A clamp receiving area is provided for receiving the clamp. A structure within the clamp receiving chamber selectively moves the clamp between the flow lumen occluding position and the non-occluding position. A non-obstructive sensor within the clamp receiving area is in a first state in response to the presence of the clamp in a selected position in the slide clamp receiving area and a second state in response to the absence of the slide clamp from the selected position. A device operatively associated with the non-obstructive sensor disables the pump in response to the non-obstructive sensor being in the second state.

The clamp can comprise a slide clamp slidable between an occluded position and a non-occluding position in response to the structure for selectively moving the clamp. The non-obstructive sensor can include a reflective pad on the clamp and a light source in the clamp receiving area directing a beam of light onto the pad. An optical sensor receives light reflected off the pad, the optical sensor being in a first state in response to receiving the selected portion of a beam of light and a second state in response to not receiving the selected portion of a beam of light. The non-obstructive sensor may further include a device for determining compatibility of the slide clamp with the sensor, the non-obstructive sensor being in a first state when the clamp is compatible with the safety apparatus and a second state when the clamp is not compatible with the safety apparatus.

The present invention further contemplates a clamp for controlling the flow of fluid through a flow lumen of an I.V. tube. The clamp includes a body and means on the body for captively receiving an outer surface of an I.V. tube in an operative position. A clamp is provided on the body for collapsing an outer surface of an I.V. tube in an operative position to thereby selectively occlude and not occlude a flow lumen of the I.V. tube. A structure is provided on the body for facilitating automated identification of the clamp.

The automated identification structure may be a surface pad which reflects a selected portion of a beam of light shined onto the pad. An optical sensor is able to identify the slide clamp based upon the reflected portion of the beam of light. The clamp can be in combination with an optical identifying structure including a lamp omitting a selected beam of light, the beam of light being directed onto the surface pad. The surface pad absorbs a portion of the beam of light and reflects a portion of the beam of light. An optical sensor receives the reflected portion of the beam of light, the optical sensor being in a first state in response to receiving the selected portion of the beam of light and a second state in response to not receiving the selected portion of the beam of light. An indicator operatively associated with the optical sensor indicates whether the optical sensor is in the first or second state.

The present invention also provides a slide clamp for selectively occluding and not occluding a flow lumen of an I.V. tube. The slide clamp has a body having oppositely facing top and bottom surfaces. A regulating aperture defined by an internal peripheral wall in the body extends transversely between the top and bottom surfaces. The regulating aperture has an occluding slot and a non-occluding passage. An I.V. tube in an operative position extending through the regulating aperture is slidable transverse to its length between the occluding slot and the non-occluding passage so that a lumen of an I.V. tube in the operative position may be selectively occluded or not occluded by sliding the I.V. tube between the occluded slot and the non-occluding passage. The peripheral wall of the aperture, when viewed in cross section, has a substantially flat I.V. tube contacting surface of a length less than the distance between the top and the bottom surfaces for minimizing friction between the I.V. tube contacting surface and an I.V. tube in the operative position as the I.V. tube is slid between the occluding slot and the non-occluding passage.

The slide clamp can further include a structure for preventing sliding of the slide clamp lengthwise of an I.V. tube in an operative position extending through the non-occluding passage solely by the force of gravity. The sliding prevention structure permits movement of the slide clamp lengthwise of the I.V. tube under application of a predetermined force greater than the force of gravity. The engaging structure may be at least two contact points, an I.V. tube extending through the non-occluding passage having an outer diameter that spans the distance between the contact points.

The slide clamp may further include indicia for facilitating automated identification of the clamp. The indicia for facilitating automated identification of the clamp may be a surface portion of the clamp, the surface portion reflecting a selected portion of a beam of light shined thereon, whereby an optical sensor receiving the reflected portion of the beam can identify the slide clamp. The slide clamp may also include oppositely facing leading and trailing edges, each having a selected width. The width of the leading edge is less than the width of the trailing edge for facilitating a selected orientation of the slide clamp prior to insertion of the slide clamp into a slide clamp receiving area. The clamp may further include first and second oppositely facing lengthwise sides, each of the sides having a notch for receiving a structure for preventing lengthwise movement of the slide clamp.

The slide clamp may be employed in combination with a safety apparatus for a pump, the safety apparatus comprising a clamp receiving area and means within the clamp receiving area for selectively sliding the slide clamp relative to an I.V. tube in the operative position between the occluding slot and the non-occluding passage.

The safety apparatus of the present invention provides a device for assuring that the flow lumen of an I.V. tube is occluded before insertion of the I.V. tube into a flow pump. Furthermore, the safety apparatus assures that the slide clamp is held in a non-occluding position during operation of the pump. Finally, the safety apparatus assures that the I.V. tube is in an occluded state prior to removal of the I.V. tube from the pump. In this manner, free flow of fluids through the I.V. tube before, during and after loading of the I.V. tube into the pump is prevented, thus minimizing the risk of a harmful bolus dose of medical fluids being inadvertently injected into a patient. Moreover, the safety apparatus assures that the slide clamp will be in a non-occluding position relative to the I.V. tube during operation of the pump.

The safety apparatus of the present invention further contemplates a slide clamp that is slidable relative to the I.V. tube under minimal frictional resistance. In this manner, smooth operation of the safety apparatus is assured. Moreover, the safety apparatus of the present invention provides a non-obstructive sensor for preventing operation of the pump if the slide clamp is not in a proper position or if a slide clamp is used with the safety apparatus which is not compatible with the safety apparatus. Thus, inadvertent use of an incompatible slide clamp with potential catastrophic results to a patient is prevented. Moreover, the non-obstructive sensor has no mechanical linkages, assuring that it will not inadvertently jam in a position indicating proper location of the slide clamp. Furthermore, the present invention provides a slide clamp having a non-occluding passage defining an I.V. tube receiving area for receiving an I.V. tube having an outer diameter slightly larger than the I.V. tube receiving area. In this manner, a slide clamp in a non-occluding position on an I.V. tube may be slid longitudinally of the I.V. tube under a force slightly greater than the force of gravity, but held in place under the force of gravity. Lastly, the present invention provides a slide clamp with a surface pad that facilitates automated identification of the slide clamp to verify that the slide clamp is compatible with a pump safety apparatus.

DETAILED DESCRIPTION OF A PREFERRED EMBODIMENT

Figure 1:
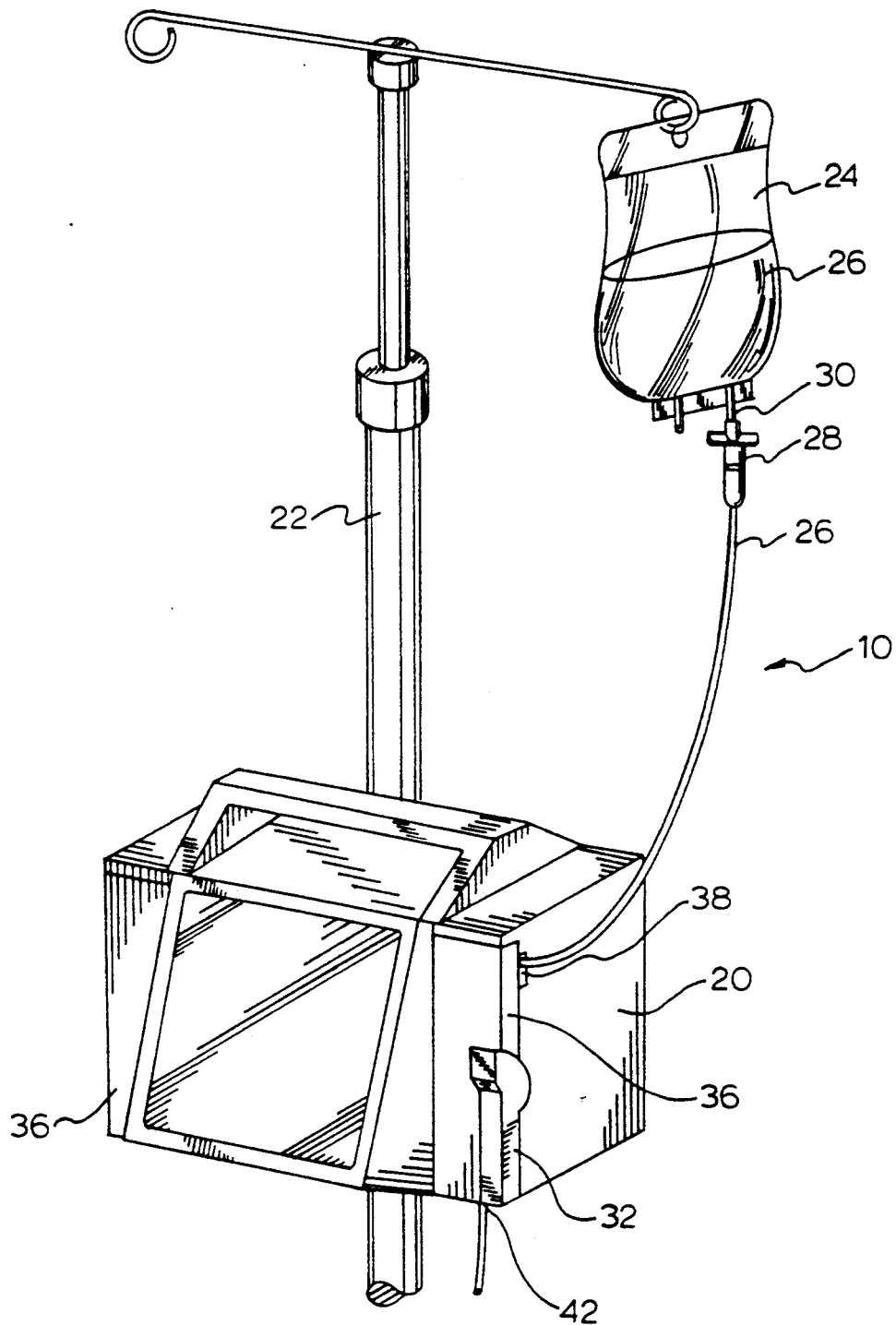
FIG. 1 is a perspective view of an intravenous pump set utilizing the safety apparatus of the present invention.

FIG. 1 is an illustration of an intravenous administration setup using a pump and a source of intravenous fluid such as a flexible container. The pump includes pump housing 20 which includes pump operating mechanics and operating electronics (not shown). The pump is mounted on an I.V. stand 22 which also serves a support for the intravenous fluid container 24. The container 24, which typically contains a fluid 26 such as saline that is administered to a patient, is also suspended from the I.V. stand 22.

An administration set 10 provides a flow path from the container 24 to the patient via the pump. The set 10 includes a segment of flexible plastic I.V. tubing 26 such as polyvinyl chloride (PVC) tubing.

The I.V. tubing 26 at its proximal end is attached to a drip chamber 28 that is in turn attached via a spike (not shown) to an outlet port 30 of the container 24. I.V. tubing 26 has connected at its distal end means for connecting the set 10 to a vein access device, such as a catheter or a needle (not shown).

The pump includes a hinged door 36 which covers the peristaltic pumping apparatus hardware. To set up the pump, the door 36 is opened, the I.V. tubing 26 is inserted into the peristaltic pump apparatus as described in detail below, the door is closed, and the pump is activated. The pump also defines apertures at the upper 38 and lower 42 peripheries of the pump housing 20 through which the I.V. tubing 26 extends when the door 36 is closed. Additionally, the door 36 includes a latch 32 which can be pivoted from a released position in which the door 36 is not locked and a latching position in which the door 36 is locked in the closed position.

While the embodiment depicted in FIG. 1 includes a dual drive peristaltic pump, the present invention contemplates use of any number of pump drives in a single peristaltic pump.

Figure 2:
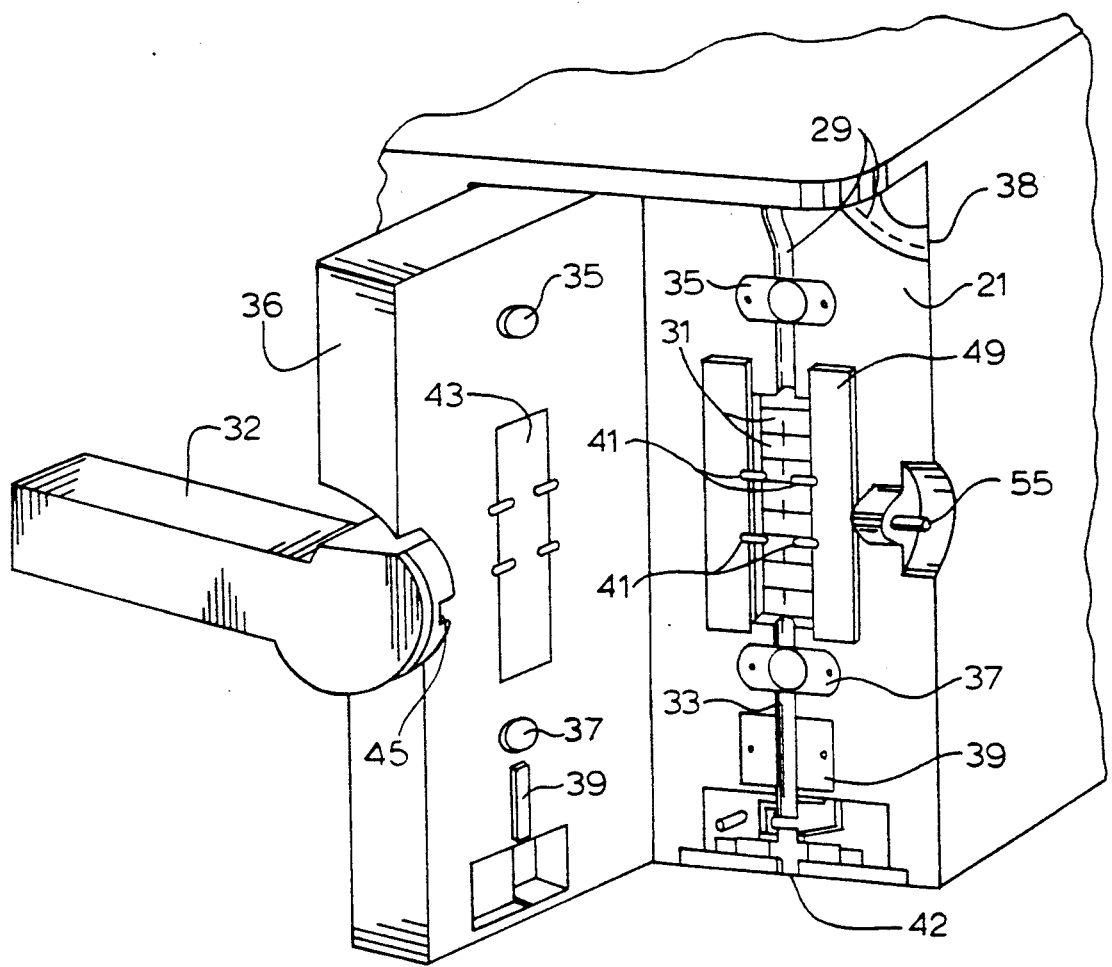
FIG. 2 is a perspective view of the peristaltic pump of FIG. 1 with a door in a open position.

Referring now to FIG. 2, the peristaltic pumping hardware is seen. An inlet groove 29 is provided leading from the access aperture 38 to a peristaltic pumping member in a form of a plurality of receptacle fingers 31. An outlet groove 33 is provided from the fingers 31 to the lower aperture 42.

An upstream occlusion sensor 35 is provided on the inlet groove 29 while a downstream occlusion sensor 37 is provided on the outlet groove 33. An air bubble detector 39 is also provided on the outlet groove 33. The door 36 of the pump includes a spring-loaded backplate 43 of conventional construction as well as the cooperating members for the upstream occlusion detector 35, downstream occlusion detector 37, and bubble detector 39. A fixed latch member 55 is provided that acts in cooperating relationship with the latch member 32 to securely latch or lock the door 36 in a closed position.

The I.V. tube 26 can be loaded into the inlet groove 29 extending straight across the reciprocal fingers 31 as guided by a plurality of I.V. tube guides 41 and into the outlet groove 33. When the door 36 is closed a catch 45 of the latch 32 mates with the fixed latch member 55 to latch or lock the door in a closed position.

Figure 3:
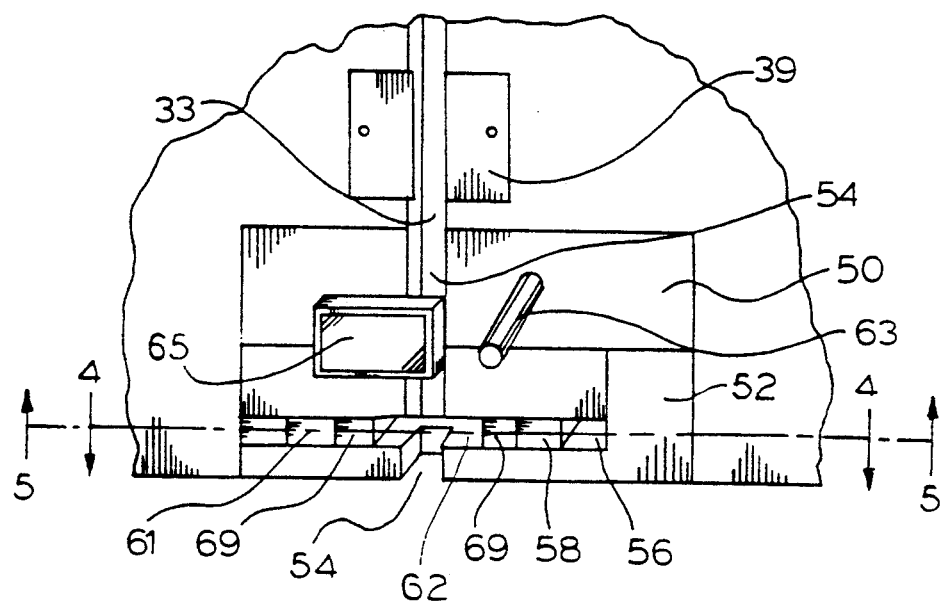
FIG. 3 is a detailed side elevational view of the safety apparatus in accordance with the principles of the present invention.

Referring now to FIG. 3, the safety apparatus of the present invention is seen in detail fixed in the lower periphery of the outlet groove 33. The safety apparatus includes an upper safety clamp housing 50 and a lower slide clamp housing, chamber 52. The safety apparatus defines as an extension of the outlet groove 33, an I.V. tube groove 54 into which the I.V. tube fits. Extending perpendicularly from the I.V. tube groove 54 is a retainer arm aperture 56 defined in the lower slide clamp housing 52. Contained in the retainer arm aperture 56 are a right cooperating retainer arm 58 and left cooperating retainer arm 61 which pivot from an open or loaded position to a retaining or unloaded position in which the distance between the two retainer arms 58,61 is smaller relative to the position of the retainer arms 58,61 in the open or loaded position. The central portion of the retainer arm aperture 56 between the cooperating retainer arms 58,61 defines the receiving area 62 for a slide clamp.

Contained on the upper safety clamp housing 50 is a release pin 63 which extends outwardly from and is capable of reciprocating into and out of the upper safety clamp housing 50. The release pin 63 activates a sliding mechanism which orients the slide clamp from an occluded to an open position.

Also contained in the safety apparatus is a safety clamp 65. The safety clamp 65 is capable of extending into the I.V. tube groove 54 to occlude the I.V. tube. The further functioning of the safety clamp 65 and release pin 63 will be described in detail below in conjunction with FIGS. 4, 5 and 6.

Referring now to FIG. 4, a cross sectional upper view of the lower slide clamp housing 52 of the safety apparatus is seen. In FIG. 4a, the slide clamp housing 52 is seen in an initial or preactivated condition.

The lower slide clamp housing 52 contains the right retainer arm 58 and the left retainer arm 61. Contained on each retainer arm 58,61 is a pivot point 67 which allows the rotational pivoting of each of the retainer arms 58,61. Further contained on the end opposite the pivot point 67 of each retainer arm 58,61 is an inwardly extending retainer finger 69 which, in cooperation with the retaining finger 69 of the cooperating retainer arm, acts to retain the slide clamp as described below. Each retainer arm 58,61 includes biasing means which, in a preferred embodiment, can be a spring 74 which pivotally biases each retainer arm 58,61 towards the cooperating retainer arm in the retained position. However, in the preactivated or loaded position, the retainer arms 58,61 are held against the bias in the open position.

The left retainer arm 61 further includes an upwardly protruding stepped portion 76 which extends upwardly into the upper safety clamp housing 50. This stepped portion 76 acts as a retaining member as will be described in detail with reference to FIG. 5.

Also contained in the lower housing is I.V. tube groove housing 78 which defines the I.V. tube groove 54. The I.V. tube groove 54 is an extension of the outlet groove 33 of the pump 20. The I.V. tube groove 54 enables the I.V. tube to be retained in the appropriate position in both the pump 20 and the safety apparatus. The I.V. tube groove 54 is located centrally between the cooperating retainer arms 58,61. This acts to center the slide clamp contained on the I.V. tube between the retainer arms 58,61.

Contained distally from the I.V. tube groove 54 is a slide member 81 which is contained on a pair of cooperating slide rails 83 which allow for inward and outward reciprocal movement of the slide member 81. The slide member 81 includes an outwardly extending biasing means which biases the slide member 81 towards the I.V. tube groove 54. In the preferred embodiment, the outwardly extending biasing means is a spring 87. The slide member 81 includes cam surfaces 89 extending outwardly on each side. The cam surfaces 89 act in cooperation with the cam followers 72 of the retainer arms 58,61 to pivot the retainer arms 58,61.

Contained between the slide rails 83 is a non-obstructive sensor 85 such as an electronic eye which can be used to sense the presence of a slide clamp. Electronic eye 85 is positioned to sense when the slide clamp has been inserted into the slide clamp receiving area. The electronic eye 85 is in electronic communication with the pump operating electronics. In the presently preferred embodiment, the electronic eye 85 senses the fully inserted slide clamp; if a fully inserted slide clamp is not sensed, the operating electronics prevents the pump from operating. The non-obstructive sensor 85 will be described in further detail below in conjunction with FIG. 12. Use of alternative embodiments such as a warning or an informational message will also be appreciated as within the scope of the present invention.

Contained extending inwardly from the slide member 81 is a slide shaft 92. The slide shaft 92 is housed in a slide shaft aperture 94 defined in the lower slide clamp housing 52 and extending inwardly from the I.V. tube groove 54. The slide shaft 92 includes a notched portion 96 defined therein. A slide latch 98 is also provided housed in a slide latch aperture 101 defined in the lower slide clamp housing 52 and extending perpendicularly to the slide shaft aperture 94. The slide latch 98 includes a cam follower 103. The slide latch 98 is biased towards the slide shaft 92 by biasing means such as a spring 105.

The slide latch 98 thus acts in conjunction with the notched portion 96 of the slide shaft 92 to retain the slide shaft 92 and thus the sliding member 81 against the outward bias of the spring 87. In the retained position, the sliding member 81 is in a loaded position while in the unretained or outward position, the sliding member 81 is in an unloaded position. It should be noted that the slide latch 98 and the notched portion 96 of the slide shaft 92 employ cooperating angled surfaces 107 which allow the slide shaft 92 to exhibit an amount of play the purpose of which will be discussed below.

Figure 4B:
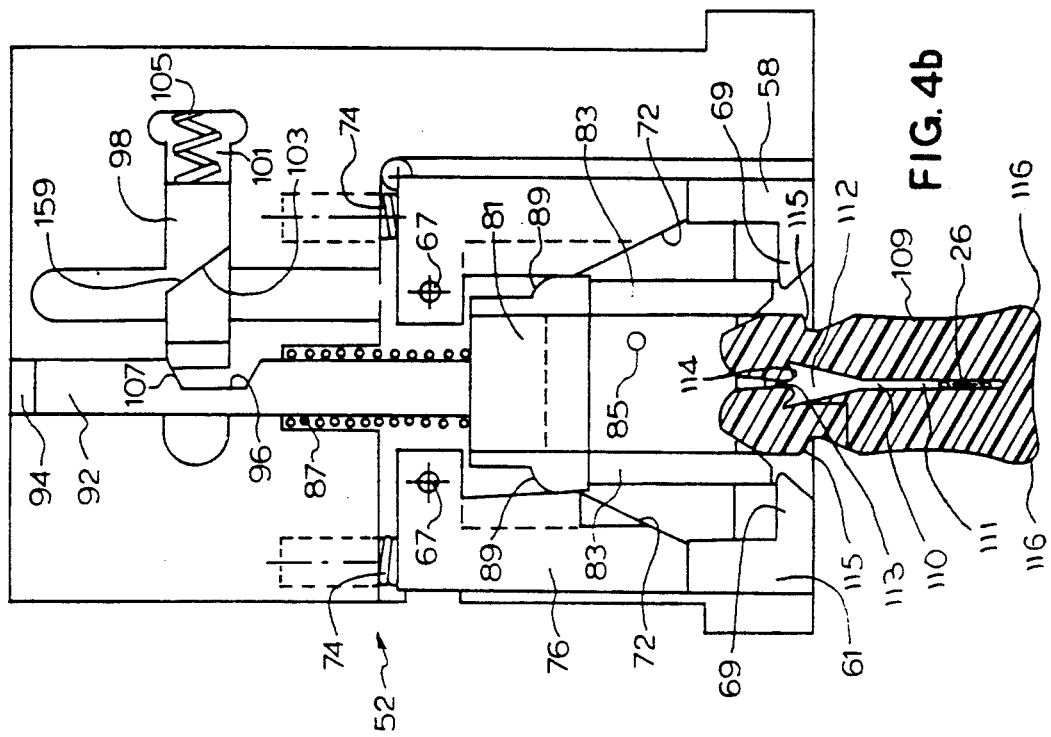
FIGS. 4a–4f are cutaway views of the apparatus of FIG. 3 taken along the line 4—4 of FIG. 3.
Figure 4A:
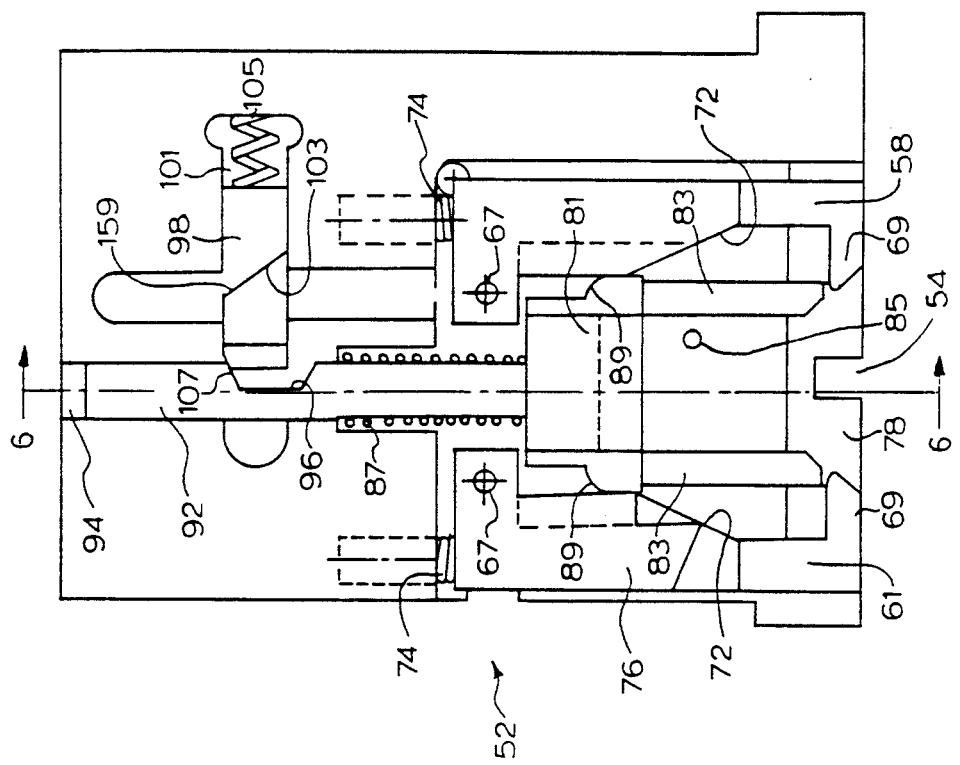

Referring now to FIG. 4b, a slide clamp 109 is shown in a position prior to insertion into the slide clamp housing 52. The slide clamp 109 includes a regulating aperture 110 which includes a thin occluding slot 111 and a wider non-occluding passage 112. The slide clamp 109 includes an access slit 113 which allows the I.V. tube 26 to be positioned into the regulating aperture 110 without requiring the slide clamp 109 to be threaded from an end of the I.V. tube 26.

The slide clamp 109 preferably includes projections 114 which extend inwardly into the non-occluding passage 112 of the regulating aperture 110. The projections 114 act to maintain frictional contact against the I.V. tube 26 when the I.V. tube 26 is in the non-occluding passage 112 in an operative position while not causing an occlusion of the I.V. tube 26. In this manner, the slide clamp 109 can be selectively positionally retained longitudinally of the I.V. tube 26 against the force of gravity yet moved longitudinally under a force in excess of the force of gravity.

The slide clamp 109 further defines notches 115 on each oppositely facing side proximal to the non-occluding portion 112 of the regulating aperture 110. These notches 115 act in cooperation with the retaining fingers 69 of the retaining arms 58,61 to secure the slide clamp 109 in the slide clamp housing 52 when the slide clamp 109 has been inserted and the retainer arms 58,61 are unloaded.

The distal portion of the slide clamp 109 is further defined by increased width outward projections 116. These outward projections 116 prevent inadvertent backward insertion of the slide clamp 109 into the slide clamp housing 52.

Figure 7:
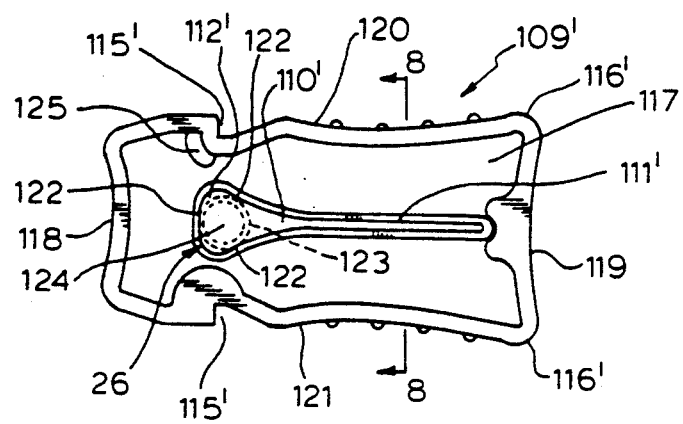
FIG. 7 is a plan view of a preferred embodiment of a slide clamp for use with the safety apparatus of the present invention.

A preferred embodiment of a slide clamp of the present invention is indicated as 109, in FIG. 7 with elements corresponding to those of the slide clamp 109 having the same reference number followed by a "'". The slide clamp 109, includes a body 117 having a leading edge 118, a trailing edge 119 and first and second oppositely facing sides 120,121. The slide clamp 109' includes a regulating aperture 110' having an occluded slot 111' and a non-occluding passage 112', all substantially identical to those of the slide clamp 109. Notches 115' are located in the first and second oppositely facing sides 120,121. Outer width projections 116' on the trailing edge 119 function in the same manner as the outward projections 116 on the slide clamp 109 to prevent inadvertent backward insertion of the slide clamp 109' into the slide clamp housing 52.

An I.V. tube 26 is illustrated in ghost lines in an operative position extending through the non-occluding passage 112' of the regulating aperture 110,. As seen in FIG. 7, the non-occluding passage 112' is configured to provide first, second and third I.V. tube contact points 122. Together the contact points 122 define an I.V. tube receiving space. The I.V. tube 26 has an outer diameter 123 equal to or slightly greater than the I.V. tube receiving space defined by the contact points 122. In this manner, the contact points 122 act to maintain frictional contact against the outer diameter 123 of the I.V. tube 26 while not causing any occlusion of the flow lumen 124 of the I.V. tube 26. The contact points 122 maintain sufficient frictional contact with the I.V. tube 26 that the slide clamp 109' cannot move longitudinally of an I.V. tube under the force of gravity, but requires a selected force in excess of the force of gravity to move the slide clamp 109' longitudinally of an I.V. tube 26.

The slide clamp 109, also includes a surface pad 125. The surface pad 125 reflects a beam of light from the non-obstructive sensor 85, as will be discussed in more detail below with reference to FIG. 12. The pad 125 is located in a precise selected position on the slide clamp 109' to insure proper cooperation with the non-obstructive sensor 85. In addition, the surface pad 125 is provided with a shiny finish (such as a No. 2 finish) to aid in reflecting a light beam transmitted by the non-obstructive sensor 85.

The top and bottom (not shown) of the slide clamp 109' are mirror images so that slide clamp 109, can be inserted into the slide clamp housing 52 with either the top or bottom orientated upward. The slide clamps 109,109' are preferably injection molded from polypropylene. The clamps could also be made from PETG, co-polyester or DELRIN. The necessary characteristics of the slide clamp material are that it be moldable within close tolerances and rigid enough to withstand pressures of up to 45 psi within the I.V. tube. Furthermore, the slide clamp material must be able to withstand EtO and gamma sterilization without impairing the functionality of the clamp.

Figure 8:
FIG. 8 is a cutaway view of the slide clamp of FIG. 7 taken along line 8—8 of FIG. 7.
Figure 8A:
FIG. 8a is an enlargement of the cutaway view of the slide clamp of FIG. 8 as indicated in FIG. 8.
Figure 9:
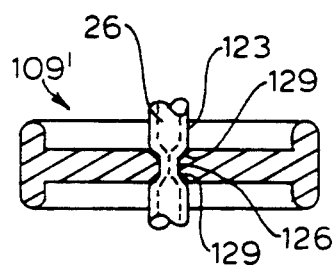
FIG. 9 is a cutaway view of the slide clamp of FIG. taken along the line 8—8 of FIG. 7 illustrating an I.V. tube disposed within the occluding slot of the slide clamp.
Figure 10:
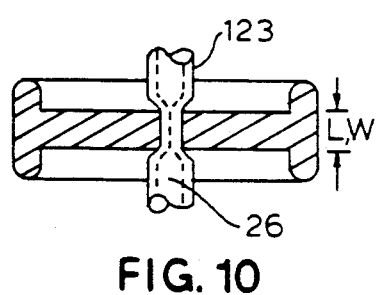
FIG. 10 is a cross-sectional view of a prior art slide clamp taken transverse to its occluding slot showing an I.V. tube disposed therein.
Figure 11:
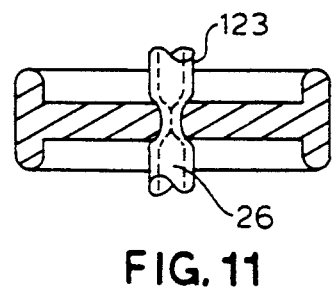
FIG. 11 is a cross-sectional view of another embodiment of a prior art slide clamp taken transverse to its occluding slot showing an I.V. tube inserted therein.

FIG. 8 illustrates in cross-section the preferred profile of the occluding slot 111'. The occluding slot has an I.V. tube contacting surface 126 of a length L less than the distance W between the top and bottom surfaces 127,128 of the slide clamp 109'. Between the top and bottom surfaces 127,128 and the I.V. contacting surface 126 are guiding surfaces 129. The guiding surfaces 129 constitute beveled edges between the I.V. contacting surface 126 and the top and bottom surfaces 127,128. The I.V. contacting surface 126 of a length L less than the distance W between the top and bottom surfaces 127,128 along with the beveled I.V. guiding surfaces 126, serve to reduce the frictional force opposing sliding of an I.V. tube between the non-occluding passage 112' and the occluding slot 111, as compared to prior slide clamps. As illustrated in FIG. 9, with this configuration substantially only the I.V. tube contacting surface 126 contacts the outer diameter 123 of an I.V. tube 26. The advantage of this structure is illustrated with reference to FIGS. 10 and 11, which show profile of prior art slide clamps. FIG. 10 illustrates a slide clamp wherein the I.V. tube contacting surface is a length L equal to the distance W between the top and bottom surfaces of a slide clamp, providing a large frictional surface to oppose sliding of the I.V. tube between the I.V. tube contacting surfaces. FIG. 26 illustrates a slide clamp having an arcuate I.V. contacting surface. As seen in FIG. 11, the entire arcuate surface contacts the I.V. tube, again creating a relatively large frictional surface to oppose movement of the I.V. tube 26 through the occluding slot. Thus, the profile illustrated in FIG. 8 permits a relatively thick body 117 for durability and sufficient rigidity to maintain the I.V. tube in an occluded state, even with the I.V. tube under high internal fluid pressure, while still allowing the slide clamp to slide transverse to the I.V. tube with minimal frictional resistance.

The I.V. contacting surface 126 has a length L of between 0.006 and 0.02 inches. Preferably, the length L is between 0.01 and 0.014 inches. The angle A between the I.V. tube contacting surface 126 and the top and bottom surfaces 127,128 must be sufficient so that the guiding surfaces 129 do not contact the I.V. tube 26.

Preferably, the angle A is in a range of between 25°–45°, with an angle of 35 being ideal.

Figure 13:
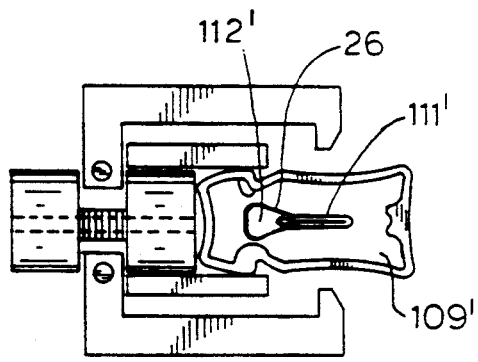
FIG. 13 is a slide clamp according to FIG. 7 with an occluding slot which is too short.
Figure 14:
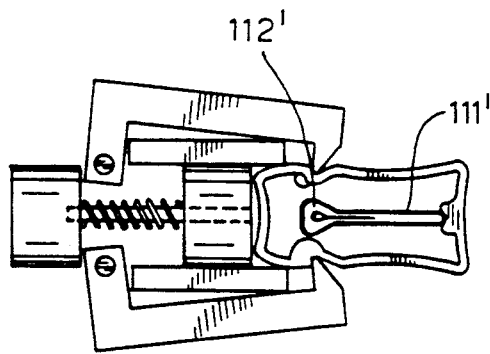
FIG. 14 is a slide clamp according to FIG. 7 with an occluding slot which is too long.

In order for a slide clamp to function properly with the safety apparatus, it must be properly dimensioned. As illustrated in FIG. 13, if the occluding slot 111' is too short the tubing 26 will not be completely occluded upon insertion of the slide clamp 109' into the safety apparatus. On the other hand if the occluding slot 111' is too long, as illustrated in FIG. 14, the tubing may not be able to slide completely into the non-occluding passage 112', leaving a partially occluded tube which will not allow medication to flow properly to a patient. In addition, the width of the occluding slot 111' is also critical. If the width is too narrow, too great a frictional force will be required to move the slide clamp relative to the I.V. tubing, inhibiting proper function of the safety apparatus. Thus, as is plainly evident by these examples, if the slide clamp is not properly dimensioned, the safety apparatus may not perform properly, creating a potential for catastrophic injury to a patient being administered medication. By way of example, acceptable slot dimensions for use with PVC tubing having a 0.102 inch inner diameter and a 0.019 inch wall thickness are as follows:

Occluding Slot Width—0.02—0.03 inches
Occluding Slot Length—0.3–0.75 inches

Of course, the required occluding slot length is a function of the non-occluding passage dimensions, the I.V. tube dimensions and the distance that the slide member 81 can travel.

Figure 12:
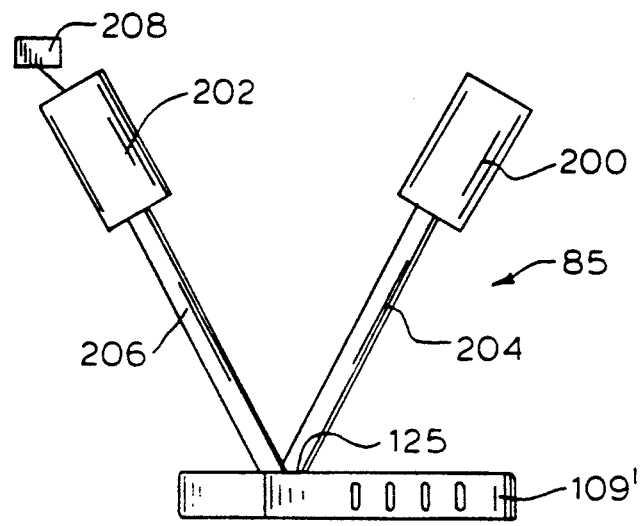
FIG. 12 is a block diagram of the optical sensor of the present invention.

FIG. 12 illustrates a preferred embodiment of the non-obstructive sensor 85. The non-obstructive sensor 85 includes an optical light source 200 and an optical light sensor 202. As illustrated in FIG. 12, the optical light source 200 emits a beam of light 204 directed onto the surface pad 125 of the I.V. clamp 109'. A portion 206 of the light beam 204 is reflected off the surface pad 125 and received by the optical light sensor 202. The optical light sensor 202 is in a first state in response to receiving a reflected light beam within a selected band width and of a selected intensity and in a second state in response to not receiving a reflected light beam within the selected intensity and band width. A switch 208 in electrical communication with the optical light sensor 202 disables the pump in response to the optical light sensor 202 being in the second state. Thus, if a slide clamp inserted into the slide clamp receiving area lacks the surface pad 125 or has a surface pad of a different size, reflectivity or light absorption, the optical sensor 202 will not be in the second state and the pump will not function. Thus, the preferred embodiment of the non-obstructive sensor 85 described herein verifies that a slide clamp inserted into the clamp receiving area is compatible with the safety apparatus. Consequently, catastrophic injury to patients resulting from the use of functionally incompatible slide clamps can be prevented.

Figure 4D:
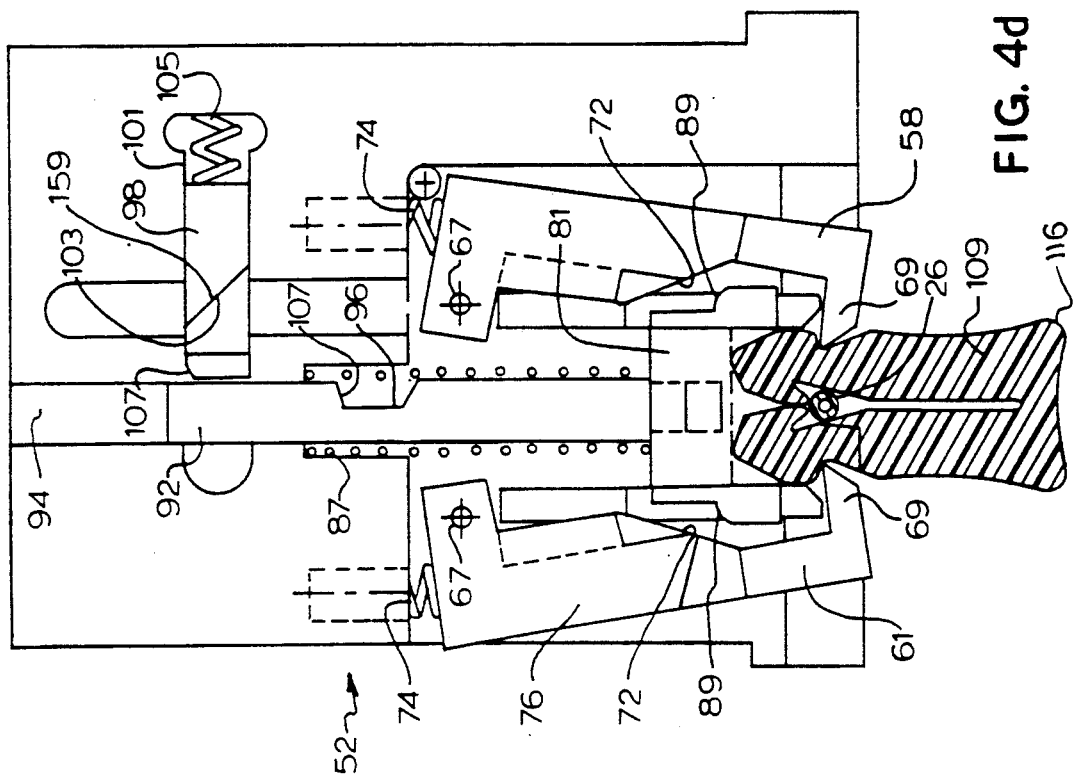
Figure 4C:
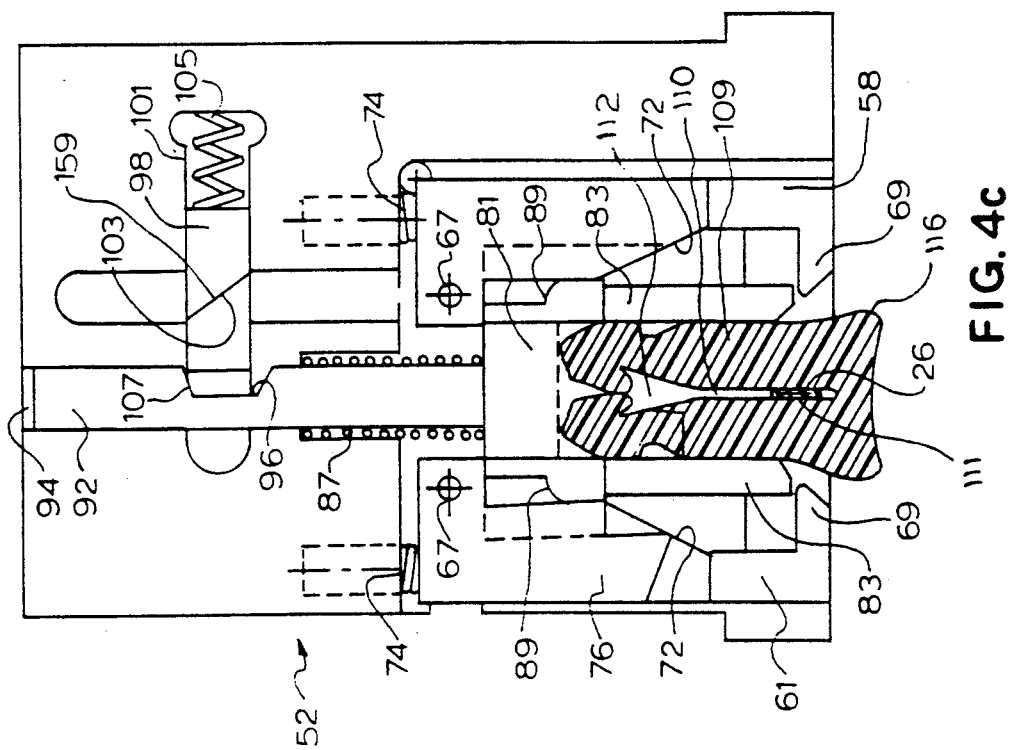
Figure 4F:
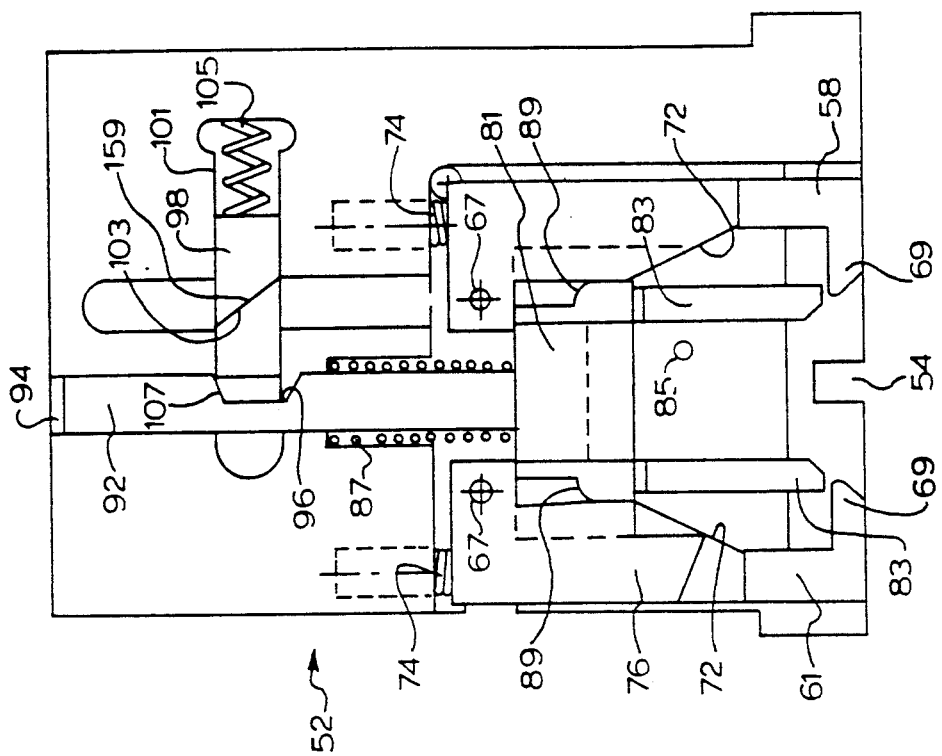

Referring now to FIG. 4c, the slide clamp 109 is shown inserted into the slide clamp housing 52. The end opposite the outward projections 116 is inserted into the slide clamp housing 52. This results in the non-occluding passage 112 of the regulating aperture 110 being inserted first. Thus, the action of the health care professional manually inserting the slide clamp 109 into the slide clamp housing 52 in conjunction with the I.V. tube groove 54 assures that, after full insertion, the I.V. tube 26 is positioned in the occluding slot 111 of the slide clamp 109.

Referring now to FIG. 5, a cutaway view of the upper safety clamp housing 50 is seen. The position of the elements of the upper safety clamp housing 50 in FIGS. 5a–5f correspond to the position of the elements of the lower slide clamp housing 50 in FIGS. 4a–4f.

The safety clamp housing 50 includes the generally L-shaped safety clamp 65. The safety clamp 65 includes an occluding member 130 which is capable of extending into the I.V. tube groove 54 and acting in cooperation with an occluding base 132 to occlude the I.V. tube 26. The generally L-shaped safety clamp 65 includes a pivot point 134 which allows the safety clamp 65 to alternatively pivot from an occluded state seen in FIG. 5e to a non-occluding state seen in FIG. 5a. At the end of the generally L-shaped safety clamp 65 opposite the occluding member 130 a latching segment 136 having a latching notch 138 is defined which acts in cooperation with a safety latch 140 which will be described in detail below.

As previously discussed with reference to FIG. 4, the left retainer arm 61 includes an upwardly protruding stepped portion 76 which extends upwardly into the upper safety clamp housing 50. The upwardly protruding stepped portion 76 of the left retaining arm 61 is oriented in the upper safety clamp housing 50 adjacent to the safety clamp 65. Thus, when the left retaining arm 61 is in the retained position, the stepped portion 76 prevents the safety clamp 65 from fully pivoting through interference with downward protruding stepped portion 200 of safety clamp 65 while when the left retaining arm 61 is in the open position, the safety clamp 65 is allowed to fully pivot.

The upper safety clamp housing 50 further includes a generally L-shaped safety latch 140. The safety latch 140 includes a pivot point 142 which allows the safety latch 140 to pivot from an engaged to a non-engaged position. The safety latch 140 and safety clamp 65 are both biased by biasing means which bias the safety clamp 65 towards the occluded position and bias the safety latch 140 towards the safety clamp 65. In a preferred embodiment, the biasing means is a spring 144 connected between a spring attachment point 146 on the upper portion of the generally L-shaped safety clamp 65 and a spring attachment point 148 on the lower portion of the generally L-shaped safety latch 140. Use of a single spring 144 in conjunction with the pivot points 134,142 and the spring attachments points 146,148 results in two different moments achieved by a single spring 144.

The safety latch 140 includes at the end opposite the spring attachment point 148 a latching mechanism 151 which acts in cooperative latching orientation with the safety clamp latching notch 138. Additionally, the safety clamp 65 and the safety latch 140 are biased by the spring 144 such that when the safety clamp 65 is in the non-occluding state, the safety latch 140 can pivot into the engaged position to catch the latching notch 138 in the safety clamp 65 to maintain the safety clamp 65 in the non-occluding state as depicted in FIG. 5c. Alternatively, when the safety clamp 65 is in the occluded state, the safety latch 140 has pivoted out of the way into the non-engaged position and is thus nonoperative so the bias of the spring 144 can maintain the safety clamp 65 in the occluded state.

Figure 5B:
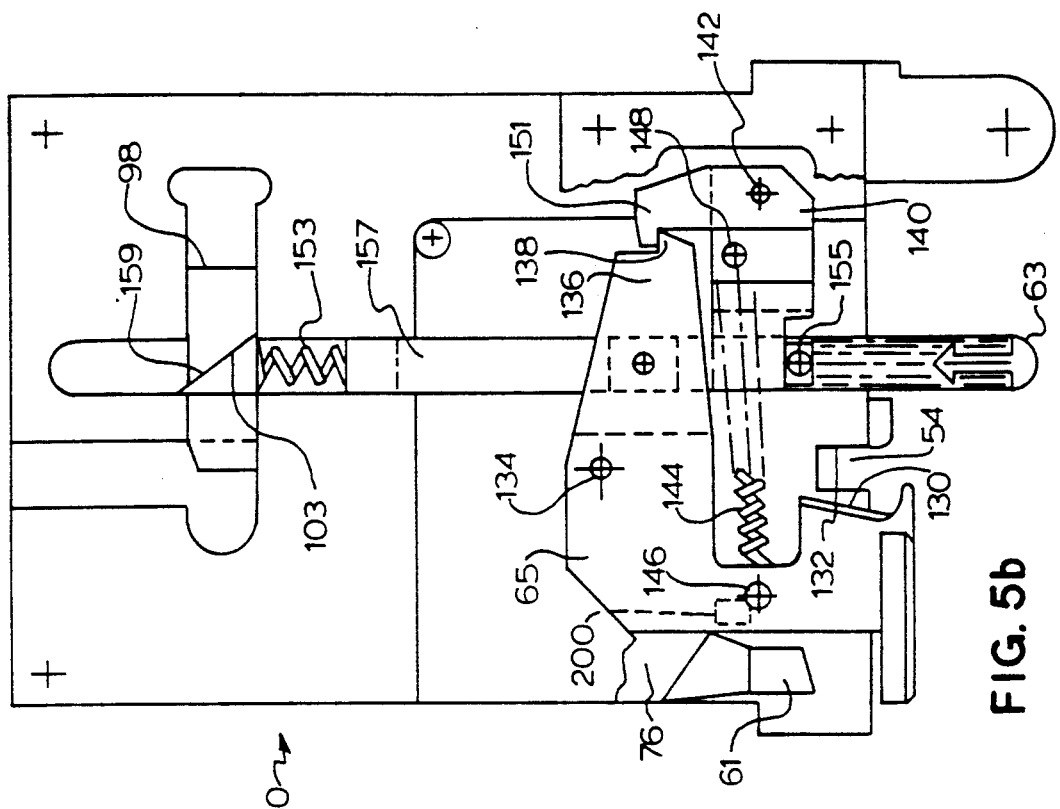
FIGS. 5a–5f are cutaway views of the apparatus of FIG. 3 taken along the line 5—5 of FIG. 3.
Figure 5A:
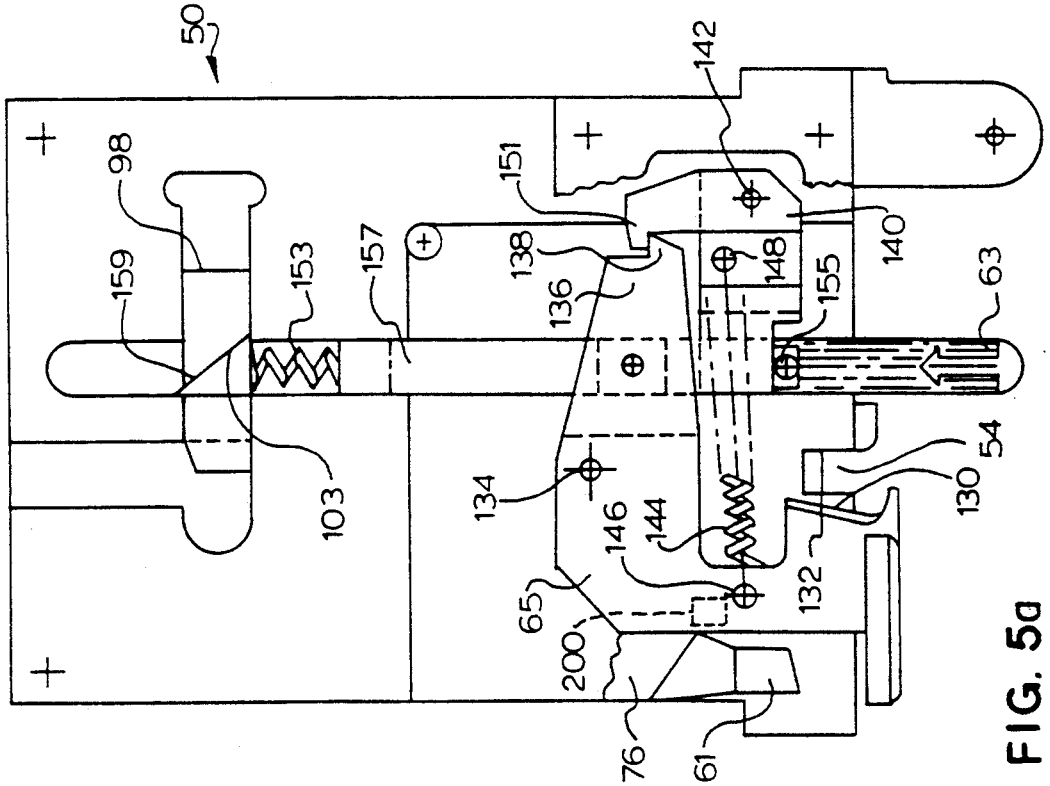

Referring to FIG. 5a, the upper safety clamp housing 50 further includes the release pin 63. The release pin 63 is outwardly biased by biasing means such as a spring 153. The release pin 63 is engaged with the safety latch by a pivot point 155 such that back and forth movement of the release pin 63 causes pivoting movement of the safety latch 140. The release pin 63 further includes a release arm 157 which includes a downwardly extending cam surface 159. The downwardly extending cam surface 159 acts cooperatively with the cam follower 103 of the slide latch 98 such that back and forth movement of the release pin 63 causes the slide latch 98 to slide.

Prior to loading the slide clamp 109 (as discussed, hereinafter the slide clamp 109 and 109, may be used interchangeably) into the lower slide clamp housing 52, the safety clamp 65 can be in either the occluded or non-occluding state. If in the occluded state, the left retainer arm 61 is in the open state which allows the safety clamp 65 to be fully pivoted to the non-occluding state. When pivoted to the non-occluding state, the safety latch 140 will catch and maintain the safety clamp 65 in the non-occluding state and the I.V. tube 26 can be loaded.

Figure 5D:
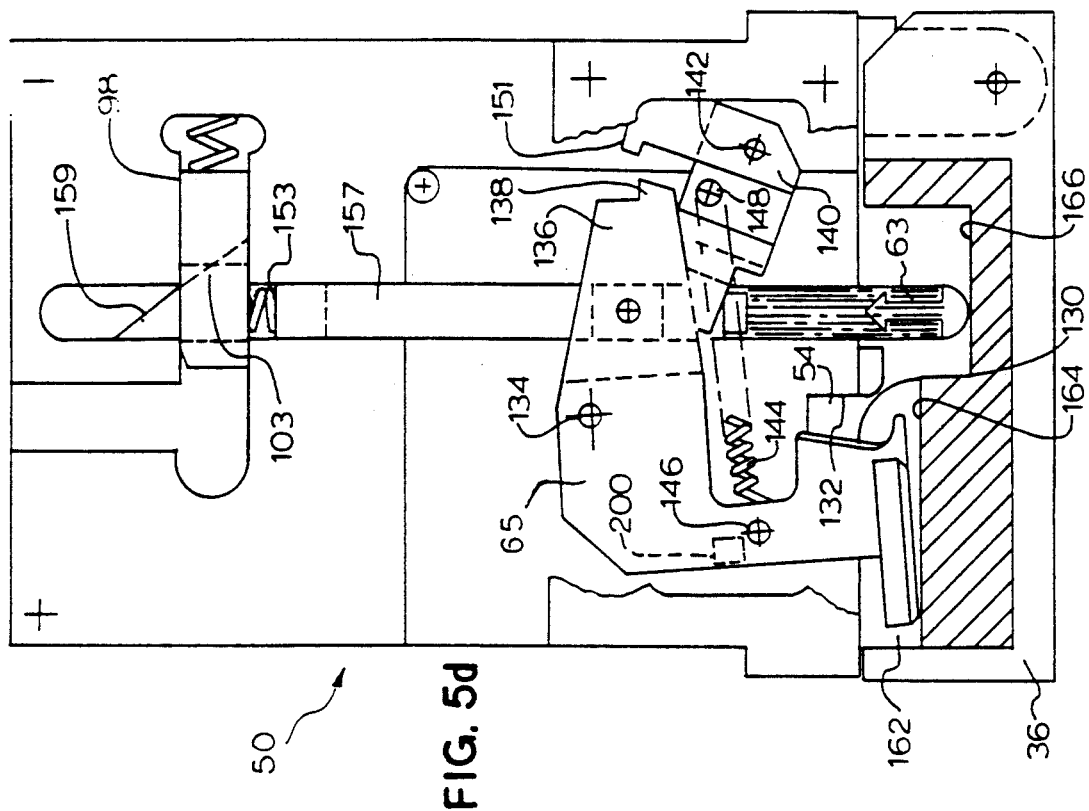
Figure 5C:
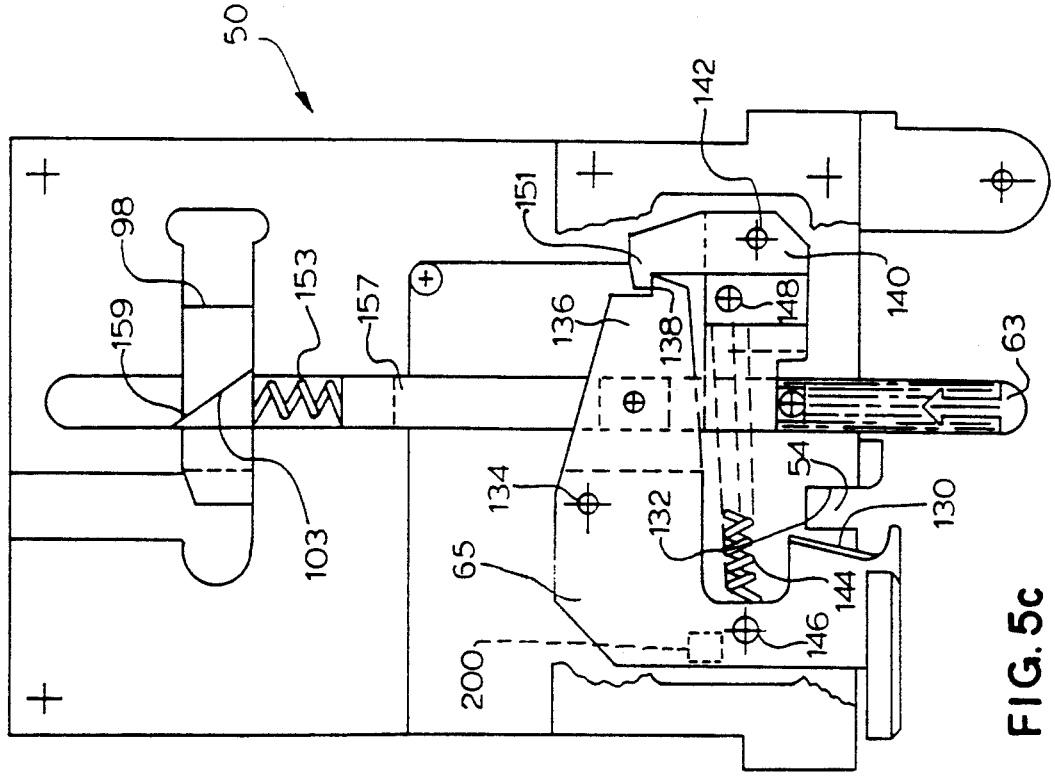

Referring to FIGS. 4c and 5c, with the I.V. tube 26 and slide clamp 109 loaded, the retainer arms 58,61 are in the loaded position and the safety clamp 65 is in the non-occluding position. The door 36 can then be closed by the health care professional as seen in FIG. 5d.

The door 36 includes a stepped inlet 162. The stepped inlet 162 includes a first stepped portion 164 corresponding to the safety clamp 65. The stepped inlet 162 includes a second stepped portion 166 corresponding to the release pin 63. The stepped portions 164,166 are sized to assure proper functional relationship with the safety clamp 65 and the release pin 63. As the door 36 is closed, the second stepped portion 166 causes the ingress of the release pin 63 which has two effects. Initially, the release pin 63 pivots the safety latch 140 thereby releasing the safety clamp 65 and causing the safety clamp 65 to return to the occluded condition. Additionally, the release arm 157 cam surface 159 acts in conjunction with the cam follower 103 of the slide latch 98 to force the slide latch 98 against the bias of the spring 105 thereby releasing the slide shaft 92 which causes the slide clamp 109 to move out to the non-occluding state. Finally, the fully closed door 36 obstructs the free pivoting of the safety clamp 65 by pressing the stepped portion 164 against the safety clamp 65. The safety clamp 65 is thereby forced into a non-occluding unlatched state.

Referring now to FIG. 4d, the position of the lower slide clamp housing 52 when the door 26 is in the closed position is seen. Initially, with the slide latch 98 cammed out of engagement with the slide shaft notched portion 96, the slide shaft 92 is biased inwardly by the spring 87 which unloads the slide member 81 thus pushing the slide clamp 109 outwardly. When this occurs, the I.V. tubing 26 is retained in the I.V. tube groove 54 by the door 36 which results in a reorientation of the I.V. tube 26 in the slide clamp 109 from the occluding slot 111 to the non-occluding passage 112 of the regulating aperture 110.

Additionally, with the slide member 81 out of the way the cooperating retainer arms 58,61 are unloaded. The fingers 69 thus latch onto the notches 115 on the slide clamp 109 and retain the slide clamp 109 with the I.V. tubing 26 in the non-occluding passage 112. Thus, in this position the slide clamp 109 allows flow of fluid through that portion of the I.V. tube 26. The safety clamp 65 is maintained in an open but not latched position by the door 36 thus allowing flow of fluid through that portio of the I.V. tube 26. The peristaltic fingers 31 are the free to provide the only occlusion or propelling motion on the contents of the I.V. tube 26.

Figure 4E:
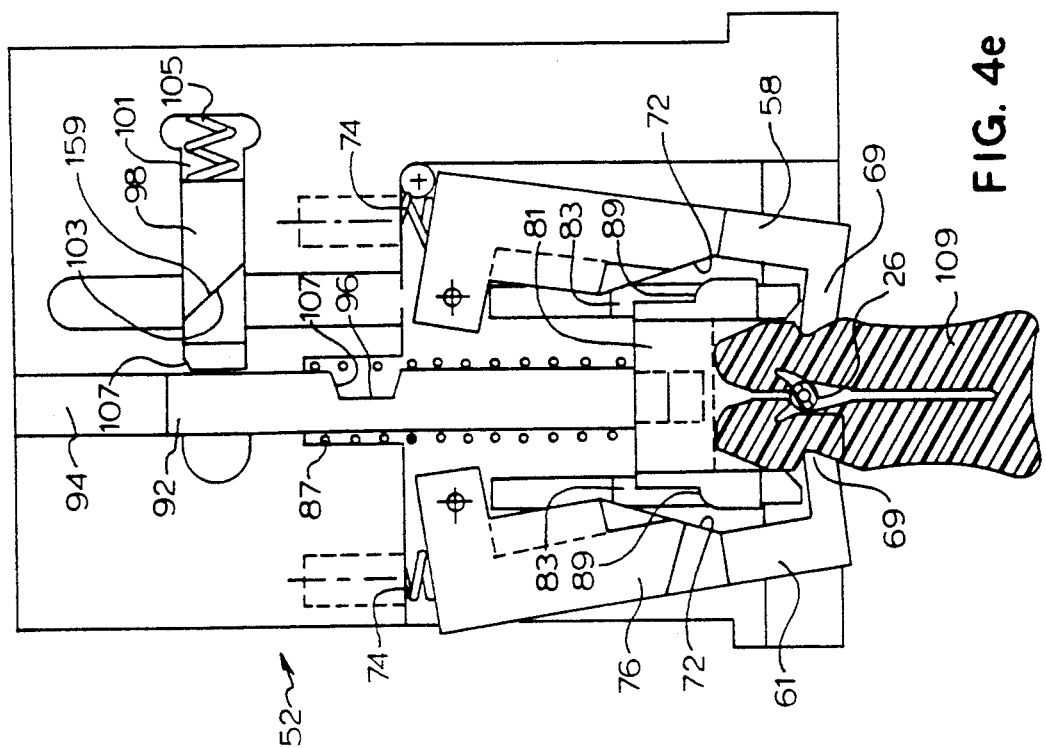
Figure 5F:
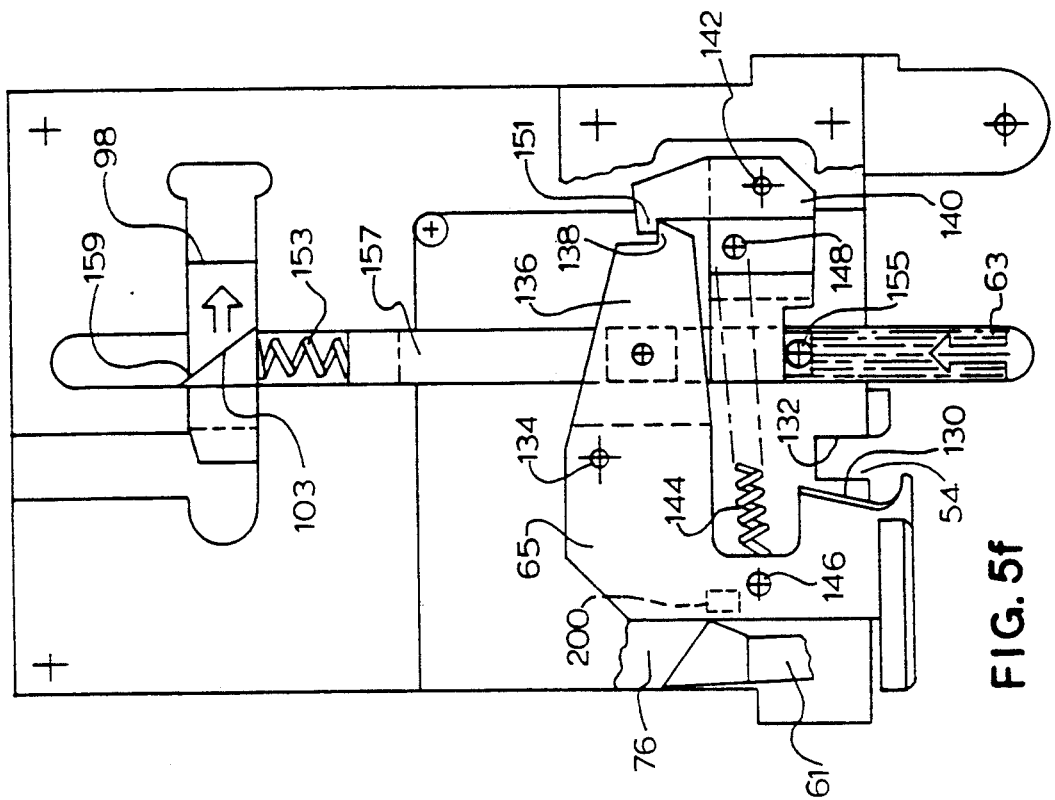
Figure 5E:
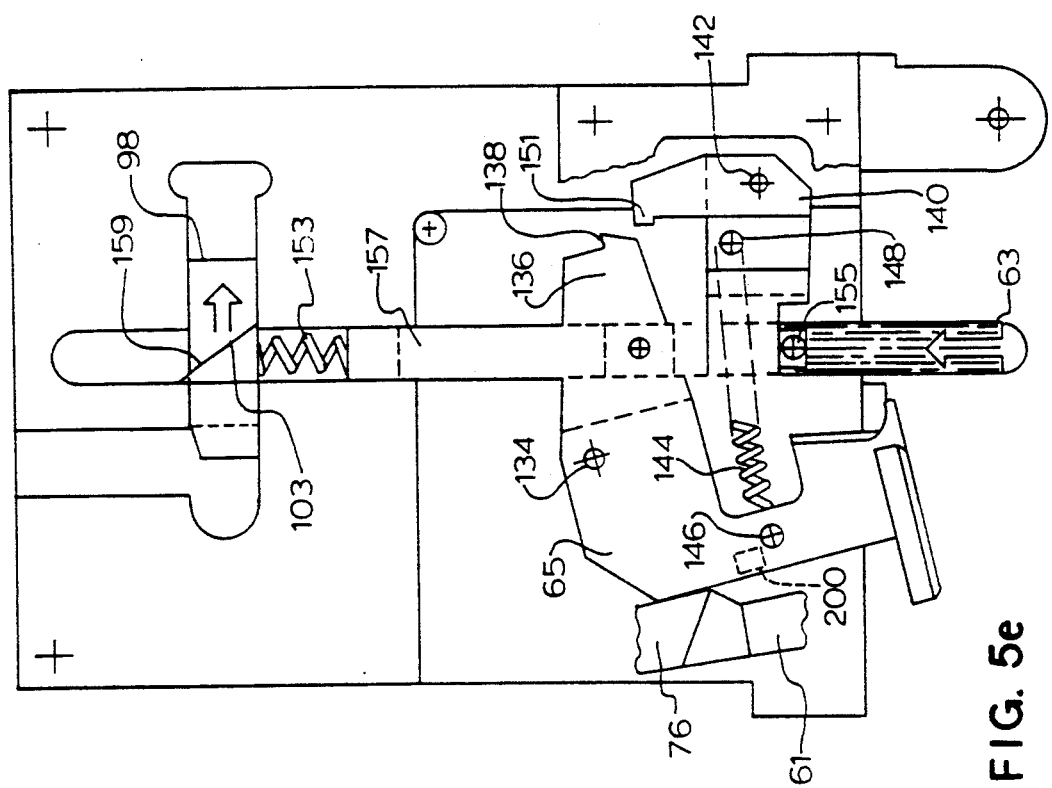

When infusion is completed and the health care professional wishes to unload the I.V. tube 26, the door 36 is opened as seen in FIGS. 4e and 5e. Opening the door 36 removes the restriction from the safety clamp 65 causing the safety clamp 65 to bias into the occluded state. This causes an immediate prevention of non-occlusion as soon as the door 36 is opened. However, if it is desired to allow non-occluding when the door 36 is in the open position, such as for example air purging, the safety clamp 65 can be manually pressed into the open but unlatched position.

Additionally, because the retainer arms 58,61 have cooperatively closed into the retain position on the slide clamp 109, the slide clamp 109 and I.V. tube 26 cannot be removed upon opening the door 36. Rather, prior to removing the slide clamp 109 and the I.V. tube 26 the health care professional is required to again insert the slide clamp 109 into the slide clamp housing 52.

Upon reinsertion of the slide clamp 109 as seen in FIGS. 4c and 5f, the forward edge of the slide clamp 109 contacts the slide member 81 which is then urged rearwardly against the forward bias of the spring 87. As the slide clamp 109 is inserted into the position seen in FIG. 4c, the slide member 81 rides on the slide rails 83 against the biasing force of the spring 87. When the slide clamp 109 is fully inserted into the slide clamp housing 52, the slide shaft 92 has been extended rearwardly such that the slide shaft notched portion 96 is located juxtapose relative to the slide latch 98 which, due to the bias of the slide latch spring 105, engages the slide shaft notched portion 96 to load the slide member 81 by preventing forward movement of the slide member 81 and therefore the slide clamp 109.

Additionally, while the slide clamp 109 is being urged rearwardly against the biasing force of the spring 87, the cam surface 89 of the slide member 81 engages against the cam follower 72 of the retainer arms 58,61 to urge into the open or loaded position the cooperating retainer arms 58,61. Thus, in this position, the I.V. tubing 26 is held in the occluding slot 111 of the regulating aperture 110 with the slide clamp 109 at rest in the slide clamp housing 52.

With the slide clamp 109 inserted into the slide clamp housing 52, the I.V. tubing 26 is again occluded by the slide clamp 109, and since the upwardly extending portion 76 of the left retainer arm 61 has pivoted out of the way of the safety clamp 65, the safety clamp 65 can be freely pivoted into an open and latched position which then and only then allows for the health care professional to remove the occluded I.V. tube 26.

Referring now to FIG. 6, an elevated cross-sectional view of the detail on the slide shaft 92 is seen. Once again the position of the slide shaft 92 in FIGS. 6a-6f corresponds to the position of the elements seen in FIGS. 4 and 5. The slide shaft aperture 94 includes an upwardly biasing means which in a preferred embodiment is spring member 165 contained in the distal portion of the slide shaft aperture 94. The aperture defines a retaining wall 167 which allows the slide shaft 92 to freely slide but which provides a stop for the spring 87 to cause the forward bias of the slide shaft 92. The slide member 81 includes a sized portion 169 on its lower periphery which is sized to accept a slide clamp 109. Additionally, extending upwardly from the sized portion is a incline portion 171 which guides the slide clamp 109 into the sized portion 169.

Figure 6A:
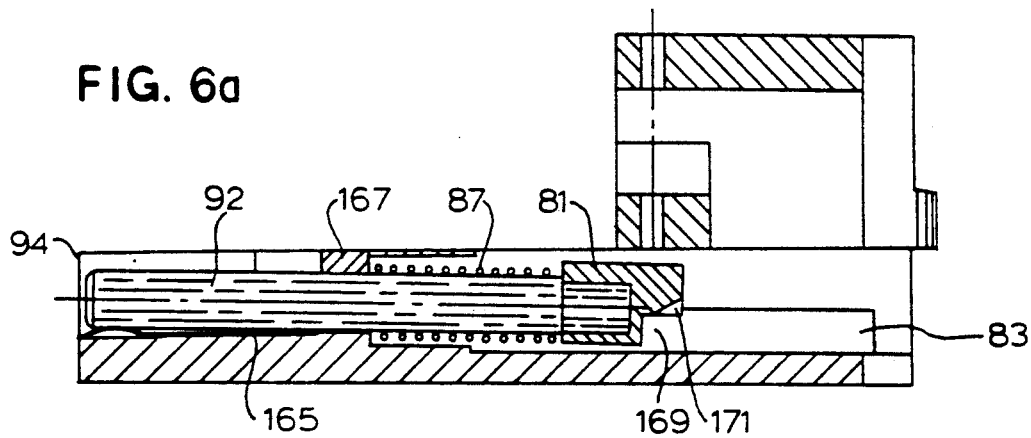
FIGS. 6a–6f are cutaway views of the apparatus of FIG. 4 taken along the lines 6—6 of FIG. 4.
Figure 6B:
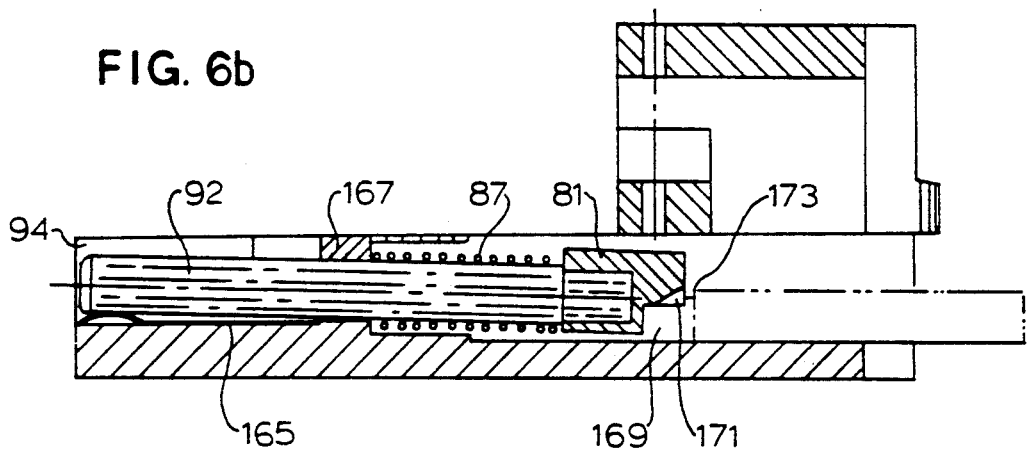
Figure 6C:
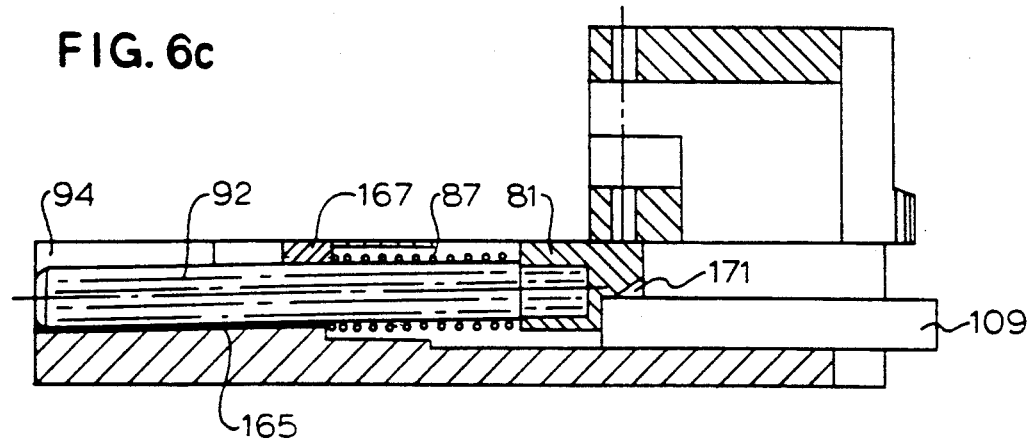
Figure 6D:
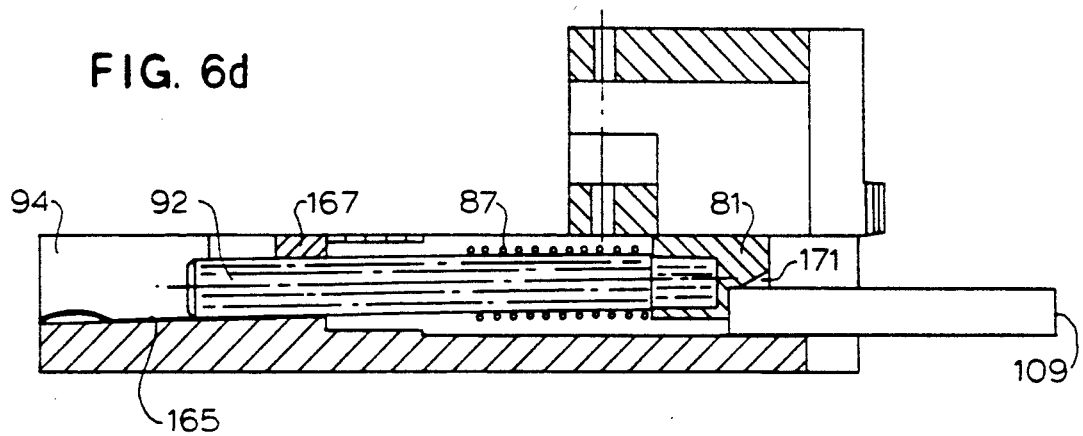
Figure 6E:
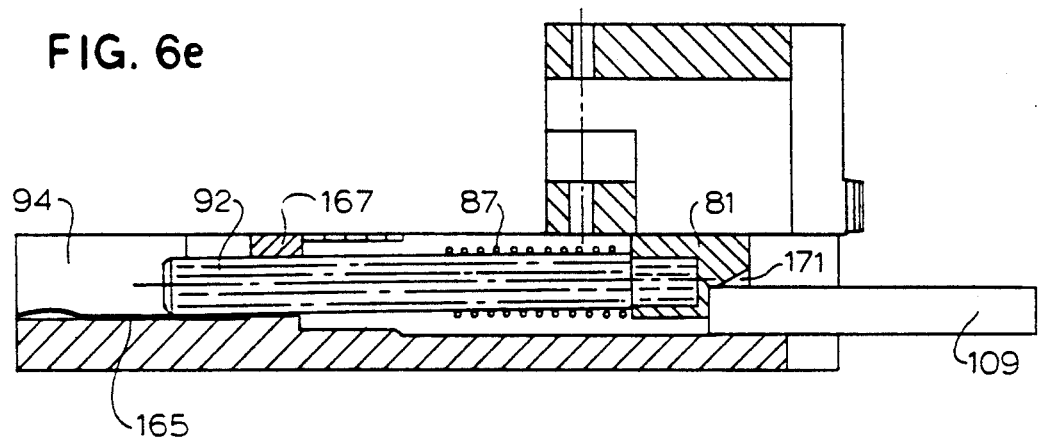
Figure 6F:
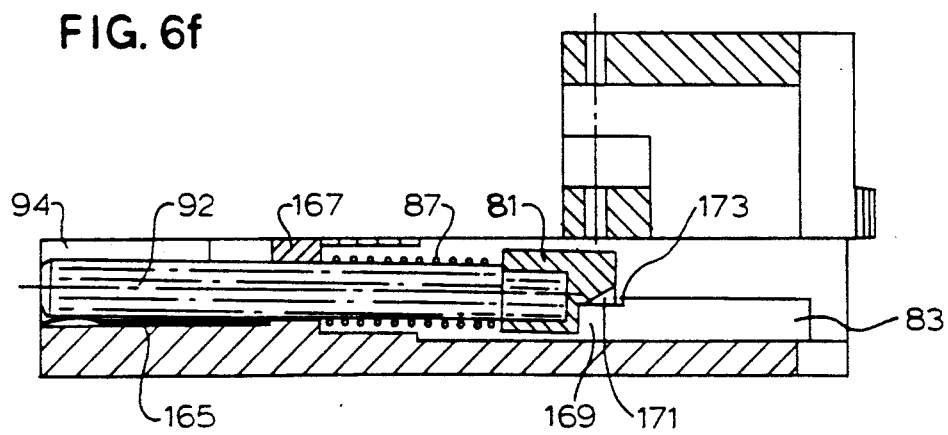

The slide rail 83 includes a stepped portion 173 best seen in FIG. 6f. The slide rail stepped portion 173 acts in conjunction with the slide member 81 to retain the slide member 81 in the rearwardly biased or loaded position. In order for the slide member 81 to become fully outwardly extended or unloaded, it is necessary for a slide clamp 109 to be inserted into the device which causes the sliding member 81 to move upwardly which allows the slide member 81 to extend past the stepped portion 173 and become unloaded.

It should also be noted that the amount of play between the fully inserted position of the slide member 81 and the position of the slide member 81 when caught on the slide rail 83 stepped portion 173 is about equivalent to the amount of play allowed by the tapered slide latch 98. As seen in FIG. 6a, when the door 36 has been closed without the presence of a slide clamp 109, thereby activating the release pin 63, the slide member 81 initially attempts to bias forward but is retained by the slide rail stepped portion 173. This is to be contrasted with FIG. 6f, in which the slide member 81 is retained by the slide latch 98 when the slide clamp 109 is inserted and the release pin 63 has not been activated.

It should be understood that various changes and modifications to the preferred embodiments will be apparent to those skilled in the art. For example, while the present invention has been described in conjunction with the peristaltic pump having pressure fingers, the principles of the present invention can also apply to a rotary-type peristaltic pump. Such changes and modifications can be made without departing from the spirit and scope of the present invention without diminishing its intended advantages. It is, therefore, intended that such changes and modifications be covered by the appended claims.

What is claimed is:

1. For use with an intravenous administration pump, a safety apparatus comprising:
    a slide clamp receiving area for receiving a slide clamp contained on I.V. tubing:
    a sliding member located within the slide clamp receiving area and being capable of sliding from an unloaded to a loaded position, the sliding member being in the loaded position when the slide clamp is in the slide clamp receiving area in an occluding position and in the unloaded position when the slide clamp is in the slide clamp receiving area in a non-occluding position;
    retainer arms contained around the slide clamp receiving area, the retainer arms being capable of retaining the slide clamp in the slide clamp receiving area; and
    a release pin cooperatively associated with the sliding member and the retainer arms such that upon activation of the release pin, the retaining arms act to retain the slide clamp in the slide clamp receiving area while the sliding mechanism unloads, thereby urging the slide clamp into a non-occluding position on the I.V. tubing while the slide clamp is retained partially within the slide clamp receiving area.

2. The apparatus of claim 1 wherein the sliding member includes a cam portion and the retainer arms include cooperating cam follower portions such that when the sliding member is loaded, the retainer arms are also loaded.

3. The apparatus of claim 1 further including an occluding biased safety clamp which is capable of occluding the I.V. tube when the inserted slide clamp is in the non-occluding position.

4. An intravenous administration pump comprising:
    housing containing operating mechanisms and electronics of the intravenous administration pump;
    a door pivotally connected to the housing;
    an I.V. tube groove defined in the housing, the I.V. tube groove being operationally positioned over a peristaltic motion mechanism such that when I.V. tubing is loaded into the I.V. tube groove, peristaltic pumping action is capable of being imparted on the I.V. tube;
    a slide clamp receiving area contained on the I.V tube groove, the slide clamp receiving area being adapted to receive a slide clamp contained on the I.V. tubing;
    an outwardly biased sliding member contained within the receiving area which upon insertion of an occluded slide clamp in the slide clamp receiving area loads;
    inwardly biased retainer arms contained around the slide clamp receiving area, the retainer arms being pivotable from a loaded to an unloaded position, the retainer arms being capable in the unloaded position of retaining the slide clamp in the receiving area; and
    a release pin cooperatively associated with the door, sliding member, and the retainer arms such that upon activation of the release pin by closing the door, the retaining arms unload to retain the slide clamp partially in the receiving area and unload the sliding member to reorient the slide clamp into a non-occluding position on the I.V. tubing.

5. The pump of claim 4 further including an occluding biased safety clamp which acts to occlude the I.V. tube when the door is open and the inserted slide clamp is in the non-occluding position.

6. The pump of claim 4 wherein the sliding member includes a cam portion and the retainer arms include cooperating cam follower portions such that when the sliding member is loaded, the retainer arms are also loaded.

7. An apparatus for preventing free flow during loading of an I.V. tube into a peristaltic pump comprising:
    a tube groove into which the I.V. tubing is positioned;
    a slide clamp receiving area into which an occluded slide clamp contained on the I.V. tubing is inserted;
    a biased sliding member which is loaded when an occluded slide clamp is in the slide clamp receiving area;
    retainer arms operatively associated with the sliding member such that when an occluded slide clamp is in the slide clamp receiving area the retainer arms are in a loaded but non-engaged position; and
    a release pin which upon activation unloads the sliding member which reorients the slide clamp from an occluded to a non-occluding position and unloads the retaining arms into an engaged position which secures the non-occluding slide clamp in the receiving area.

8. The apparatus of claim 7 wherein the sliding member includes a cam portion and the retainer arms include cooperating cam follower portions such that when the sliding member is loaded, the retainer arms are also loaded.

9. The apparatus of claim 7 further including an occluding biased safety clamp which is capable of occluding the I.V. tube when the inserted slide clamp is in the non-occluding position.

* * * * *

UNITED STATES PATENT AND TRADEMARK OFFICE
CERTIFICATE OF CORRECTION

PATENT NO. : 5,290,239
DATED : March 1, 1994
INVENTOR(S) : Eric Myren

It is certified that error appears in the above-indentified patent and that said Letters Patent is hereby corrected as shown below:

On the title page, item [75] Inventors:

change

"Donald J. Classey, Waukegan; Theresa Grajo, Round Lake Beach; Kenneth Lynn, McHenry; John McVey, Lake Zurich; Eric Myren, Barrington; Gabriel Vebovsky, McHenry, all of Ill."

to

--Eric Myren, Barrington, Ill.--

Signed and Sealed this

Twenty-third Day of May, 1995

Attest:

BRUCE LEHMAN

Attesting Officer        Commissioner of Patents and Trademarks